United States Patent [19]

Nezu

[11] Patent Number: 5,827,726
[45] Date of Patent: Oct. 27, 1998

[54] DNA CODING PROTEIN KINASE

[75] Inventor: Jun-ichi Nezu, Shizuoka-ken, Japan

[73] Assignee: Chugai Seiyaku Kabushiki Kaisha, Tokyo, Japan

[21] Appl. No.: 913,050

[22] PCT Filed: Mar. 15, 1996

[86] PCT No.: PCT/JP96/00660

§ 371 Date: Sep. 5, 1997

§ 102(e) Date: Sep. 5, 1997

[87] PCT Pub. No.: WO96/28554

PCT Pub. Date: Sep. 19, 1996

[30] Foreign Application Priority Data

Mar. 16, 1995 [JP] Japan ........................................ 7-57104

[51] Int. Cl.$^6$ ............................. C12N 1/21; C12N 15/12; C12N 15/70; C07H 21/04
[52] U.S. Cl. ................................. 435/252.33; 435/320.1; 536/23.2; 536/23.5; 536/24.31
[58] Field of Search ................................. 435/91.1, 91.2, 435/252.3, 320.1, 325, 252.33; 536/23.1, 23.2, 23.5, 24.31

[56] References Cited

PUBLICATIONS

W.J. Fantl et al., "Signalling by Receptor Tyrosine Kinases", Annu. Rev. Biochem., vol. 62, pp. 453–481, 1993.

J.B. Bolen, "Nonreceptor Tyrosine Protein Kinases", Oncogene, vol. 8, pp. 2025–2031, Mar. 31, 1993.

R.J. Davis, "The Mitogen–Activated Protein Kinase Signal Transduction Pathway", The Journal of Biological Chemistry, vol. 268, No. 20, pp. 14553–14556, Jul. 15, 1993.

P. Nurse, "Universal Control Mechanism Regulating Onset of M–Phase", Nature, vol. 344, pp. 503–508, Apr. 5, 1990.

J. Pines, "Arresting Developments In Cell–Cycle Control", Trends. Biochem. Sci., vol. 19, pp. 143–145, Apr. 19, 1994.

D. Carling et al., "Mammalian AMP–Activated Protein Kinase Is Homologous to Yeast and Plant Protein Kinases Involved in the Regulation of Carbon Metabolism", The Journal of Biological Chemistry, vol. 269, No. 15, pp. 11442–11448, Apr. 15, 1994.

S.K. Hanks et al., "The Protein Kinase Family: Conserved Features and Deduced Phylogeny of the Catalytic Domains", Science, vol. 241, pp. 42–52, Jul. 1, 1988.

S.K. Hanks, "Homology Probing: Identification of cDNA Clones encoding Members of the Protein–Serine Kinase Family", Proc. Natll. Acad. Sci. USA, vol. 84, pp. 388–392, Jan., 1987.

L. Tamagnone et al., "BMX, a Novel Nonreceptor Tyrosine Kinase Gene of the BTK/ITK/TEC/TXK Family Located In Chromosome Xp22.2", Oncogene, vol. 9, pp. 3683–3688, 1994.

M.R. Mark et al., "rse, a Novel Receptor–Type Tyrosine Kinase With Homology to Axl/Ufo, Is Expressed at High Levels in the Brain", The Journal of Biological Chemistry, vol. 269, No. 14, pp. 10720–10728, Apr. 8, 1994.

K. Ohashi et al., "Cloning of the cDNA for a Novel Receptor Tyrosine Kinase, Sky, Predominantly Expressed In Brain", Oncogene, vol. 9, pp. 699–705, 1994.

T. Karn et al., "Structure, Expression and Chromosomal Mapping of TKT From Man and Mouse: a New Subclass of Receptor Tyrosine Kinases With a Factor VIII–Like Domain", Oncogene, vol. 8, No. 12, pp. 3433–3440, 1993.

*Primary Examiner*—George C. Elliott
*Assistant Examiner*—Robert Schwartzman
*Attorney, Agent, or Firm*—Browdy and Neimark

[57] ABSTRACT

The invention provides a DNA comprising a base sequence encoding an amino acid sequence for a novel protein kinase, a plasmid containing the DNA, a transformant transformed with the plasmid, a process for producing the DNA, and oligonucleotide which hybridizes with the base sequence encoding a novel protein kinase.

10 Claims, 1 Drawing Sheet pancreas
kidney
skeletal muscle
liver
lung
placenta
brain
heart peripheral blood leukocyte
colon
small intestine
ovary
testis
prostate
thymus
spleen fetal kidney
fetal liver
fetal lung
fetal brain G361
A549
SW480
Raji
MOLT-4
K-562
HeLa S3
HL-60

↑ 3kb

DNA CODING PROTEIN KINASE

This application is a 371 of PCT/JP96/00660 filed Mar. 15, 1996.

TECHNICAL FIELD

This invention relates to a novel DNA containing the consensus sequence of a protein kinase catalytic domain. More specifically, the invention relates to a novel DNA containing a catalytic domain consensus sequence characteristics of serine/threonine kinase. The invention also relates to a plasmid containing said DNA, a transformant having said plasmid, a process for producing said DNA, and an oligonucleotide capable of specific hybridization with said DNA.

BACKGROUND ART

The studies on the mechanism of signal transduction into eukaryotic cells in response to external stimuli have seen a rapid progress in recent years.

For instance, it has been unravelled that intracellular signal transduction is accomplished by a complex kinase-cascaded signal transduction system in response to stimulation by growth factors such as a nerve growth factor (NGF) and an epidermal growth factor (EGF) and it is known that a growth factor receptor which is a kind of tyrosine kinases and an MAP kinase family which is a kind of serine/threonine kinases are both involved in the transduction mechanism (Williams, L.T. et al., Annu. Rev. Biochem., 1993, 62, 453–481; Boleu, J. B. Oncogene, 1993, 8, 2025–2031; Davis, R. J., J. Biol. Chem., 268, 1993, 14553–14556). It is also known that the phosphorylation and dephosphorylation of proteins with enzymes belonging to a cycline-dependent kinase (CDK) family which is a kind of serine/threonine kinases are involved in the regulation of cell cycles and studies on the details of the mechanism are in progress (Nurse, P., Nature, 344, 503–508, 1990; Pines, J., Trends Biochem. Sci., 19, 143–145, 1994).

In addition, an SNF1 gene is known as one of the genes believed to play an important role in the metabolism of saccharides in yeast cells.

Further in addition, it has recently been reported that an AMP activated protein kinase (AMPK) gene cloned from the rat liver shows a high level of homology in amino acid sequence to the SNF1 gene (Carling, D. et al., J. Biol. Chem., 1994, 269, 11442–11448). It is found that the AMPK inactivates enzymes such as acetyl CoA carboxylase which catalyzes the first step of fatty acid synthesis, 3-hydroxy-3-methylglutaryl CoA reductase which is a key enzyme to the biosynthesis of cholesterol and other isoprenoid compounds, and hormone-sensitive lipase in a way of phosphorylation and it is considered to be one of the important regulatory factors in lipid metabolisms including the metabolism of triglycerides or cholesterol esters (Clarke, P. R. et al., EMBO J., 1990, 9, 2439–2446). Thus, it has been suggested that the SNF1 family is heavily involved in the metabolic regulation of carbon compounds such as saccharides or lipids in eukaryotic cells.

As described above, many reports have suggested that the phosphorylation and dephosphorylation of proteins have important roles in the adjustment of various cell functions and it has also been reported that similarities exist in the structures of catalytic domains of the participating protein kinases (Steven K. Hanks et al., Science, 1998, Vol. 241, pp. 42–52).

In recent years, the cloning of cDNAs of novel protein kinases by methods utilizing the above-noted structural similarties of protein kinases has been described in many reports (see, for example, Holtzman, D. et al., Proc. Natl. Acad. Sci. USA, 1987, 84, 8325–8329; Hanks, S. K., Proc. Natl. Acad. Sci. USA, 1987, 84 388–393; and Andrew F. Wilks, Proc. Natl. Acad. Sci. USA, 1989, vol. 86, pp. 1603–1607). With the advances in the studies in the field of interest, the analysis of the functions of novel protein kinase genes is in progress and the mechanisms of some important intracellular signal transduction are being elucidated but it can hardly be said that all mechanisms have been completely unravelled.

DISCLOSURE OF INVENTION

As described above, protein kinases obviously have diverse roles to play within cells. Therefore, isolating and identifying a novel protein kinase gene are expected to be useful for various purposes such as unravelling the mechanism of signal transduction within cells and the development of therapeutics of diseases due, for example, to abnormal activities of the protein kinase encoded by the gene.

An object of the invention is to provide a DNA encoding a novel protein kinase, a plasmid having said DNA and a transformant obtained by transforming a host with said plasmid. Another object of the invention is to provide a process for producing said DNA. Yet another object of the invention is to provide an antisense DNA capable of specific hybridization with the sequence of said DNA by synthesizing an oligonucleotide based on the sequence of said DNA.

The present inventors synthesized oligonucleotides based on the amino acid sequence of a region conserved as a common feature to certain kinds of protein kinases and screened human fetal liver derived cDNAs by means of a PCR method using the synthesized oligonucleotides as primers, thereby successfully isolating a cDNA encoding a novel protein kinase. This has led to the accomplishment of the present invention.

Thus, the present invention provides a novel DNA encoding a protein kinase. Specifically, the present invention provides a DNA comprising a base sequence encoding the amino acid sequence set forth under SEQ. ID. NO. 7 in the Sequence Listing, or a base sequence which has an insertion, deletion or substitution added to a portion of said base sequence encoding the amino acid sequence of SEQ. ID. NO. 7, or base sequence hybridizing with either of said base sequences.

According to an embodiment of the present invention, there is provided a DNA comprising the base sequence set forth under SEQ. ID. NO. 2 in the Sequence Listing.

The present invention further provides a plasmid having said protein kinase coding DNA.

The present invention further provides transformants obtained by transforming prokaryotic or eukaryotic cells with a plasmid having said protein kinase coding DNA.

The present invention further provides a process for producing said protein kinase coding DNA, which comprises the steps of:

(1) synthesizing cDNAs from human-derived mRNAs with reverse transcriptase;

(2) performing PCR using as templates the cDNAs syhthesized in step (1) and using as primers oligonucleotides based on the amino acid sequence of a region conserved as a common feature to certain kinds of protein kinases; and (3) isolating positive clones by screening a cDNA library containing long-stranded cDNAs using as probes the clones obtained in step (2).

The present invention further provides an oligonucleotide capable of specific hybridization with a base sequence encoding the amino acid sequence set forth under SEQ. ID. NO.7 in the Sequence Listing.

BEST MODE FOR CARRYING OUT THE INVENTION

Figure 1:
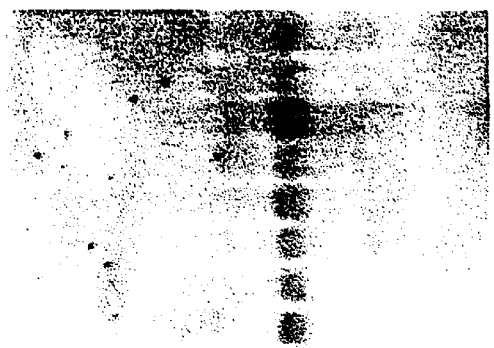
FIG. 1 shows the result of Northern blot analysis of pLKB-1.

The protein kinase gene of the invention encodes a sequence of 433 amino acids and has a 1302-bp base sequence including a stop codon.

The DNA containing a gene encoding the amino acid sequence set forth under SEQ. ID. NO. 7 in the Sequence Listing may typically be prepared by the following procedure.

First, poly(A)$^+$ RNA is isolated from an organ of interest. In the example to be described below, a human fetal liver was used; however, as long as the gene of interest is expressed, the starting material is not limited in any particular way. The isolation of RNA from the organ may be performed by common procedures known to the skilled artisan, as exemplified by a guanidinium thiocyanate/hot phenol method, a guanidinium/cesium chloride method and a guanidinium hydrochloride method. The greater part of the thus obtained RNA fractions comprise rRNA and tRNA which do not encode proteins and many of the mRNAs present in the cytoplasm of eukaryotic cells are known to have a poly(A) sequence at the 3' end; hence, only poly(A)$^+$ RNA is adsorbed on an oligo(dT)-cellulose column and then eluted to isolate the pure form of poly(A)$^+$ RNA. Commercial grades of ploy(A)$^+$ RNA derived from various organs are currently available (as from CLONTECH Inc.) and may be substituted.

Subsequently, with the thus obtained poly(A)$^+$ RNA used as a template, cDNAs are synthesized for use as templates in PCR. For the synthesis of cDNA, common procedures known to the skilled artisan for preparing cDNA libraries may be employed. Generally, a mixture comprising poly (A)$^+$ RNA, reverse transcriptase, primers (e.g. oligo (dT) primer and random primer) and a buffer solution is incubated at an appropriate temperature to synthesize a first cDNA strand; then, RNase and DNA polymerase are added and the mixture is incubated at an appropriate temperature to synthesize a second CDNA strand. In the usual case, the resulting double-stranded cDNA is cloned into an appropriate vector to prepare a cDNA library; in the present invention, the thus obtained cDNAs may be directly used as templates to perform screening by PCR.

PCR (polymerase chain reaction) is a method in which a cycle consisting of three steps, denaturation of the template DNA, annealing of primers to a single strand of the template DNA and extension of a complementary strand to the single-stranded template DNA starting from the annealed primers, is repeated to amplify the DNA fragment in the region held between the two primers.

As is apparent from this operating principle, the DNA sequence to be obtained (amplified) by PCR is largely dependent on the primers used and, hence, determination of the primer sequence is an important problem. Since one of the objects of the present invention is to isolate a novel protein kinase gene, the present inventors noted the amino acid sequence of a region conserved as a common feature to certain kinds of protein kinases. They synthesized mixed primers T1 and T2 containing all codons that correspond to said amino acid sequence and used them in the example to be described hereinafter.

PCR may be performed by usual procedures. Specifically, a mixed solution containing a template DNA, primers, a mixture of dNTPs, a buffer solution and Taq polymerase may be subjected to 20–40 repeated cycles each consisting of incubations at a denaturation temperature (typically 94°–96° C.) for 0.5–1 min, at an annealing temperature (typically 37°–60° C.) for 0.5–2 min, and at an extension temperature (typically 60°–72° C.) for 0.5–3 min. If necessary, different cycles may be combined.

The clones amplified by PCR are anticipated to contain the sequences of the employed primers at their termini. Hence, in order to check whether the clones obtained are novel, the PCR product may be subcloned into an appropriate vector and thereafter sequenced. In the present invention, a clone was obtained that had a novel DNA sequence as set forth under SEQ. ID. NO. 1 in the Sequence Listing given below. This clone had an overall length of 186 bp and an open reading frame composed of 62 amino acid residues could be taken out of this DNA sequence.

Further in the present invention, cloning of longer cDNAs was attempted in order to investigate the structure of a more integral gene. The procedure of this cloning will be described below.

In order to clone longer cDNAs, short fragments of cDNA from the cDNA library to be screened is preferably removed from the viewpoint of screening efficiency. Hence, in the present invention, the above-described procedure was repeated to synthesize double-stranded cDNAs from human fetal liver poly(A)$^+$ RNAs and thereafter subjected to size fractionation by agarose gel electrophoresis so as to recover only cDNAs of about 1 kbp or more, which were used to prepare the cDNA library to be screened. Size fractionation may be performed prior to the synthesis of double-stranded cDNAs, namely, at the stage of poly(A)$^+$ RNAs; in this alternative case, only RNA stretches beyond certain lengths can be recovered by suitable methods such as electrophoresis and precipitation using sucrose density gradients.

From the thus fractionated double-stranded cDNAs, a cDNA library can be prepared by various procedures known to the skilled artisan. In the example to be described below, a Lambda ZAP$^R$ II vector system (Stratagene) was used from such viewpoints as the convenience of procedures in subsequent sequencing; needless to say, this is not the sole case of the invention.

In the next step, the clone obtained by the previous step of PCR which contained the novel DNA sequence is used as a probe to screen the cDNA library, thereby attempting to isolate a clone encoding a more integral gene. Screening of the cDNA library may be performed by the ordinary plaque hybridization method which is commonly known to the skilled artisan. Further, in order to remove false positive plaques which can potentially be acquired in this plaque hybridization (primary screening) step, secondary screening may be performed either by repeating plaque hybridization or by applying PCR from such viewpoints as the ease of operations.

Subsequently, the insert (the portion containing the gene of interest) in each of the resulting positive clones is subcloned into a suitable plasmid vector to be preserved as a plasmid. The vector for cloning is not limited in any particular way and may be selected as appropriate for the purpose of subsequent operations. If desired, a suitable host may be transformed with the plasmid to prepare transformants for subsequent preservation. The host to be transformed is not limited to any particular type as long as it is capable of conserving the plasmid stably and may appropriately be selected from among eukaryotic and prokaryotic cells depending upon the purpose of subsequent operations. *E. coli* is generally used as the host.

Since there exist in principle more than one codon which is composed of three base pairs to encode one amino acid, many DNA sequences exist for encoding a certain amino acid sequence. This is also true with the gene that has been shown by the present inventors to encode the amino acid sequence of a novel protein kinase and it should be noted that many possibilities exist for DNA sequences other than that of the native gene derived from human fetal liver which has been elucidated in the present invention. Thus, the DNA sequence of the present invention is in no way limited to the native human derived DNA sequence but embraces other DNA sequences encoding the amino acid sequence of the novel protein kinase elucidated in the present invention.

As is well known in the gene recombinant technology, a certain DNA sequence may be mutated without greatly changing its intrinsic characteristics (the protein kinase activity in the case of the present invention) of the protein encoded by the DNA sequence or in such a way as to improve said characteristics. Therefore, any skilled artisan can occasionally perform artificial insertion, deletion or substitution on the DNA to be provided by the present invention without greatly changing its intrinsic characteristics or in such a way as to improve said characteristics. The present invention also embraces such mutant genes.

The present invention further provides a DNA containing a base sequence that hybridizes either with a base sequence encoding the amino acid sequence set forth under SEQ. ID. NO. 7 in the Sequence Listing or with a base sequence obtained by adding an insertion, deletion or a substitution to a portion of that base sequence in the manner described above. Hybridization may be performed by applying commonly adopted conditions for plaque hybridization (as described in Maniatis, T. et al., Molecular Cloning, Cold Spring Harbor Lab., 1989).

Further in addition, an antisense DNA can be prepared on the basis of a base sequence encoding the amino acid sequence set forth under SEQ. ID. NO. 7 in the Sequence Listing according to the invention. An antisense DNA is a DNA that has a base sequence complementary to the mRNA generated by transcription from the DNA sequence of the invention. When incorporated into a cell, the antisence DNA may occasionally react with the mRNA to form a hybrid, thereby retarding the synthesis of the final product protein. The present invention also provides an oligonucleotide capable of specific hybridization with a DNA sequence encoding the amino acid sequence set forth under SEQ. ID. NO. 2 in the Sequence Listing.

The term "oligonucleotide" as used above should be understood in its broadest sense. Thus, it covers both (1) oligonucleotides containing naturally occurring bases and sugar portions bound by phosphodiester bonds, and (2) oligonucleotide analogues which function in similar ways to the oligonucleotides (1) but which have non-naturally occurring portions. Exemplary oligonulceotide analogues include those oligonycleotides which have been chemically modified in the phosphate groups, sugar portions, 3' and 5' ends with a view to providing improved stability. If desired, phosphodiester bonds may be replaced by nonionic and nonchiral other structures. Also included within the category of oligonucleotide analogues are those oligonucleotides which contain modified bases, namely, purine or pyrimidine other than those which occur naturally.

The length of oligonucleotides to be provided by the present invention is not limited in any particular way but they have preferably 8–40, more preferably 15–30, subunits (one subunit is a combination of a base and a sugar and adjacent subunits are bound by phosphodiester bonds and the like).

Preferred target sites of the mRNA with which the oligonucleotides to be provided by the present invention will hybridize include a transfer initiation site, a translation initiation site, an intron/exon binding site and a 5' capping site. Considering the secondary structure of the mRNA, it is more preferred to select sites with little or no steric hindrance.

The oligonucleotides of the present invention can be produced by synthesis methods known to the skilled artisan, for example, by a solid-phase synthesis method using a DNA synthesizer typically available from Applied Biosystems. Oligonucleotide analogues can also be produced by similar procedures (Akira Murakami et al., "Synthesis of Functional Antisense DNA" in Yuki Goseikagaku, 48(3): 180–193, 1990).

EXAMPLE

The following example is provided for the purpose of further illustrating the present invention but is in no way to be taken as limiting.
(A) Searching for Novel Clones by PCR Using the cDNAs Derived from Human Fetal Liver Poly(A)⁺ RNA as templates:
A-1. Synthesis of PCR primers:

The inventors asked Sawady Technoloby Co., Lt. to synthesize oligonucleotides T1 and T2 having the following sequences determined on the basis of the amino acid sequence of a region conserved as a common feature to certain kinds of protein kinases. The prepared mixture of T1 and T2 primers was used as a primer in PCR. The base sequence of T1 primer is set forth under SEQ. ID. NO. 3 in the Sequence Listing and that of T2 primer is set forth under SEQ. ID. NO. 4 in the Sequence Listing.

T1:5' end-GT(AGTC)GC(AGTC)GT(AGTC)AA(AG)ATG(TC)T(AGTC)-AA-3'-end(SEQ ID NO:3)

T2:5' end-TC(AGTC)CC(AG)TA(AG)CA(AG)CA(AG)TA(TC)TC-3'-end (SEQ 1D NO:4)

A-2. Preparation of templates for PCR:

Using a TimeSaver™ cDNA synthesis kit (Pharmacia), cDNAs were synthesized from the poly(A)⁺RNA of human fetal liver (CLONTECH) in accordance with the attached manual; the synthesized cDNAs were used as templates for PCR.

The specific procedures were as follows. Human fetal liver poly(A)⁺ RNA (5 µg) thermally denatured by warming at 65° C. for 10 min was added to a reaction solution for first-strand synthesis consisting of murine reverse transcriptase, random hexamer primer and a reaction buffer solution and the mixture was incubated at 37° C. for 1 hour to synthesize the first cDNA strand. The reaction solution was subsequently added to a reaction solution for second-strand synthesis consisting of *E. coli* derived RNaseH, *E. coli* derived DNA polymerase I and a reaction buffer solution and the mixture was incubated first at 12° C. for 30 min, then at 22° C. for 1 hour to synthesize the second CDNA strand. The reaction mixture was subjected to phenol/chloroform extraction to remove proteins, then subjected to ethanol precipitation to recover the synthesized cDNAs, which were dissolved in 50 μL of TE buffer solution (Tris-HCl, 10 mM; EDTA, 1 mM; pH 8.0) and used as template DNA for PCR.

A-3. Searching for novel DNA by PCR:

The primers synthesized in A-1 and the template DNA prepared in A-2 were incorporated in a reaction solution of the following recipe and PCR was performed with this solution.

Reaction Solution:
Template DNA: 2.5 μL (out of 50 μL of the DNA solution prepared in A-2)
T1 primer: 200 pmol
T2 primer: 200 pmol
dNTPs: each dNTP at a final concentration of 0.2 mM
Tap polumerase: 2.5 U
10×buffer solution: 10 μL
Sterilized water: to make 100 μL After denaturation at 94° C. for 6 min, PCR was performed through 40 cycles, each consisting of denaturation at 94° C. for 1 min, annealing at 48° C. for 1 min and extension at 72° C. for 2 min.

A-4. Subcloning and sequencing of PCR product:

After agarose gel electrophoresis of the PCR product obtained in A-3, a band of a predicted size (ca. 180 bp) was excised and DNA was recovered by the glass beads method using Sephaglas™ BandPrep kit (Pharmacia). Using SureClone™ ligation kit (Pharmacia), the recovered DNA was subcloned into a plasmid vector as follows in accordance with the attached manual.

First, a Klenow fragment, polynucleotide kinase and 10×reaction buffer solution (2 μL) were added to the recovered DNA (ca. 100 ng); the mixture was diluted with sterilized water to a total volume of 20 μL and incubated at 37° C. for 30 min to make both terminals of the DNA blunt-ended and phosphorylate the 5' end.

To the thus conditioned DNA, pUC18 vector (50 ng) dephosphorylated after cleavage with SmaI, T4DNA ligase, DTT and 2×reaction buffer solution (10 μL) were added; the mixture was diluted with sterilized water to a total volume of 20 μL and incubated at 16° C. for 2 hours to effect ligation. Using a quarter of the reaction solution (5 μL), competent E. coli strain JM109 (available from Wako Pure Chemical Industries Co., Ltd.) was transformed in accordance with common procedures known to the skilled artisan (as described in Maniatis, T. et al., Molecular Cloning, Cold Spring Harbor Lab., 1989).

The transformed E. coli cells were sown on an LB plate containing ampicillin (100 μg/mL), X-Gal (5-bromo-4-chloro-3-indoyl-β-D-galactoside: 40 μg/mL) and IPTG (isopropyl-β-D-thiogalactopyranoside; 0.1 mM) and incubated at 37° C. overnight. From the colonies growing on the LB plate, 44 white colonies presumably harboring plasmid DNAs containing inserts were selected and the plasmid DNAs were extracted and the inserts were sequenced in the manner to be described below.

The extraction of plasmid DNAs from the white colonies was performed using QIAprep-spin kit (Funakoshi) in accordance with the common alkali SDS method described in the attached manual. With the extracted template plasmid DNAs, the base sequences of the inserts were determined as follows by cycle sequencing with PRISM™ Terminator Mix (Applied Biosystems).

To about 1 μg of the DNAs, a sequencing primer (3.3 pmol) and PRISM™ Termination Mix (9.5 μL) were added and the mixture was diluted to a total volume of 20 μL and subjected to 25 cycles of PCR, each cycle consisting of reactions at 96° C.×30 sec, 50° C.×15 sec and 60° C.×4 min. The excess primer and the fluorescent dye in the reaction solution were removed either by gel filtration on MicroSpin™ S-200HR column (Pharmacia) or by several extractions with phenol/chloroform, and the DNAs were recovered by ethanol precipitation. The base sequences of the recovered DNAs were determined by electrophoresis and analysis with an Applied Biosystems model 373A Sequencer.

A-5. Analysis of clones:

Thirty of the 44 selected clones had an identical sequence to a known protein kinase with the reported structure; however, the other 14 clones were verified to have an identical but yet to be reported novel sequence. One of such clones was designated LKB-1, having the base sequence set forth under SEQ. ID. NO. 1 in the Sequence Listing.

The base sequence of LKB-1 had an open reading frame region consisting of 186 bases and it encoded 62 amino acids (SEQ ID NO:8).

In the next place, an attempt was made to isolate longer clones from the cDNA library constructed from human fetal liver poly(A)$^+$ RNA.

(B) Isolation and Structural Analysis of Long Stranded Clones of LKB-1:

B-1. Preparation of cDNA library derived from human fetal liver poly(A)$^+$ RNA:

Double-stranded cDNAs were synthesized from human fetal liver poly(A)$^+$ RNA as in A-2 using TimeSaver™ cDNA synthesis kit, except that the poly(A)$^+$ RNA was used in an amount of 2 μg and that an oligo(dT)$_{12-18}$ primer was used for first-strand syntheis. The synthesized double-stranded cDNAs were fractionated for size by agarose electrophoresis and only the cDNAs having sizes of at least about 1 kbp were recovered. An EcoRI/NotI adaptor was linked to the cDNA ends and the unreacted adaptor in the reaction solution was removed with a spun column and the remainder was incorporated into a preliminarily EcoRI cleaved and dephosphorylated Lambda ZAP$^R$ II vector (Stratagene). E. coli strain XL1-Blue was used as a host. The cDNAs incorporated into the vector were packaged using GIGAPACK$^R$ II PACKAGING EXTRACT (Stratagene) in accordance with the attached manual. Stated specifically, a freeze/thaw extract, a sonic extract and the incorporated cDNAs were mixed and incubated at 22° C. for 2 hours to effect packaging, thereby yielding a cDNA library.

B-2. Screening of the CDNA library:

Primary screening of the cDNA library was performed by plaque hybridization in accordance with the customary procedures described in the literature (e.g. Maniatis, T. et al., Molecular Cloning, Cold Spring Harbor Lab., 1989).

Specifically, about 2×10$^5$ phage particles were sown on an LB agar plate and the resulting plaques were transferred to Hybond-N filter (Amersham), alkali denatured and illuminated with UV light to immobilize the DNA on the filter. The filter was then incubated in a hybridization solution (50% formamide, 4×SSC, 50 mM of HEPES, pH 7.0, 10×Denhardt's solution, 100 μg/mL of thermally denatured salmon sperm DNA) at 42° C. for 3 hours to effect prehybridization. Subsequently, hybridization was performed by incubation at 42° C. for at least 16 hours together with $^{32}$P labelled and thermally denatured probes (inserts in LKB-1).

The probes were radiolabelled using Random Primer DNA labelling kit (Ver. 2 of Takara Shuzo Co., Ltd.) in accordance with the attached manual. Specifically, about 100 ng of the insert isolated in pure form by agarose gel electrophoresis was denatured thermally; thereafter, T1 and T2 primers (each 20 pmol), a Klenow fragment and 50 μCi of [α-$^{32}$P]dCTP (3000 Ci/mmol) were added to a solution containing the thermally denatured LKB-1 insert DNA and the mixture was incubated at 37° C. for 30 min to prepare labelled probes.

After the hybridization, the filter was washed with washing solution A (2×SSC, 0.1% SDS) twice at room temperature for 15 min, subsequently with washing solution B (0.5×SSC, 0.1% SDS) first at 50° C. for 20 min, then at 55° C. for 20 min, and finally with washing solution C (0.2× SSC, 0.1% SDS) at 60° C. for 20 min. After the washing operations, the filter was dried and subjected to autoradiography.

As a result of such screening of about 2×10$^5$ pfu of phage clones, three positive signals were obtained.

A single-plaque derived phage suspension was prepared from the suspension of phage particles containing the positive clones obtained by the primary screening and the thus prepared phage suspension was used to perform secondary screening by PCR under the conditions set forth below. For use in the PCR, the following two primers were prepared. Their sequences were based on the sequence of the DNA in the LKB-1 insert. The base sequence of S2 primer is set forth under SEQ. ID. NO. 5 in the Sequence Listing and that of A1 primer is set forth under SEQ. ID. NO. 6 in the Sequence Listing.

S2: 5'-TGAAGAAGAAGAAGTTGCGAAGGA—3'(SEQ ID NO:5)
A1: 5'-CCACCAGCTGGATGACATTTTGT—3'(SEQ ID NO:6)
PCR reaction solution:
  Phage suspension: 2 μL
  S2 primer: 50 pmol
  A1 primer: 50 pmol
  dNTPs: each dNTP at a final concentration of 0.2 mM
  Taq polymerase: 1.25 U
  10×buffer solution: 5 μL
  Sterilized water to make: 50 μL After denaturation at 94° C. for 6 min, PCR was performed through 40 cycles, each consisting of denaturation at 94° C. for 1 min, annealing at 50° C. for 1 min and extension at 72° C. for 2 min.

The PCR product was subjected to agarose gel electrophoresis and two phage clones producing a band of the predicted size (ca. 100 bp) were found positive.

B-3. Subcloning of positive phase clones into plasmid vector:

The positive phage clones were excised into a plasmid (pBluescript$^R$ SK(-) vector) by an ExAssist™ TM/SOLR™ system using a helper phage ExAssist and *E. coli* strain SOLR. In accordance with the manual attached to PREDIGESTED LAMBDA ZAP$^R$ II/EcoRI/CIAP cloning kit (Stratagene), *E. coli* strain Xl1-Blue was infected with the positive phage clones and the helper phage and cultivated at 37° C. for 2.5 hours so that the plasmid excised into the culture solution was incorporated into *E. coli* strain SOLR. The resulting clones were designated pLKB1-1 and pLKB1-2.

The inserts in the pLKB1-1 and pLKB1-2 were analyzed for base sequence as in A-4, therby determining the base sequence of the novel protein kinase of the invention (pLKB-1). The determined sequence is set forth under SEQ. ID. NO. 2 in the Sequence Listing.

B-4. Structural analysis of pLKB-1:

The base sequence of pLKB-1 contained an open reading frame encoding 433 amino acids. The pLKB-1 also had sequences that agreed with the consensus sequences of an ATP binding domain and a protein kinase catalytic domain as set forth below.

Homology with the consensus sequence of ATP binding domain:
ATP binding domain consensus sequence:
  [Leu, Ile, Val]-Gly-Xaa-Gly-Xaa-[Phe, Tyr, Met]-[Ser, Gly]-Xaa-Val (SEQ ID NO:9)
pLKB-1 sequence:
  Leu-Gly-Glu-Gly-Ser-Tyr-Gly-Lys-Val corresponding to residues 55–63 of SEQ ID NO:7)

Homology with the consensus sequence of protein kinase catalytic domain:
Protein kinase catalytic domain consensus sequence:
  [1]-Xaa-[His, Tyr]-Xaa-Asp-[2]-Lys-Xaa-Xaa-Asn-[1]-[1]-[1] (SEQ ID NO:10)
pLKB-1 sequence:
  Ile-Val-His-Lys-Asp-Ile-Lys-Pro-Gly-Asn-Leu-Leu-Leu corresponding to residues 172–184 of SEQ ID NO:7 (where [1] represents [Leu, Ile, Val, Met, Phe, Tyr, Cys]; [2] represents [Leu, Ile, Val, Met, Phe, Tyr]; Xaa represents any amino acid).

With respect to the base sequence set forth under SEQ. ID. NO. 2 in the Sequence Listing, a homology search was conducted against the GenBank$^R$ database by the Lipman-Pearson method (Lipman, D. J. et al., Scinece 227, 1985, 1435–1441); the proteins which were found to have the highest level of homology (on the order of 30%) were AMPK belonging to the SNF1 gene family, MPA kinase, etc.

As described above, pLKB-1 had sequences in agreement with various known consensus sequences and in other areas, it also contained a region in agreement with a sequence highly conserved in a known protein kinase; in view of these facts it may as well be said that the protein encoded by pLKB-1 is a novel protein kinase.

As set forth above, the consensus sequence of a protein kinase catalytic domain has lysine (Lys) at position 7 and it is well known that this is a characteristic feature of serine/threonine kinase. It is also known that thyrosine kinase is characterized by having either one of arginine, serine, threonine, alanine and cysteine at the same position 7. Therefore, the protein encoded by pLKB-1 can safely be considered to be serine/threonine protein kinase.

*E. coli* harboring the thus obtained clone pLKB-1 containing the base sequence set forth under SEQ. ID. NO. 2 in the Sequence Listing was internationally deposited, under accession Number FERM BP-5035, with the National Institute of Bioscience and Human-Technology, Agency of Industrial Science and Technology, 1–3, Higashi 1 chome, Tsukuba-shi, Ibaraki-ken 305, Japan on Mar. 7, 1995.

(C) Northern Blot Analysis of pLKB-1

Nylon membranes on which poly(A)$^+$ RNAs as prepared from various human organs and cultured cell lines have been transferred and immobilized are available from CLONTECH Inc. and are extensively used when studying the expression distribution of certain genes in humans. The inventor therefore purchased such membranes (Human Multiple Tissue Northern Blot.Human, Human II, Human Fetal II and Human Cancer Cell Line) from CLONETECH and performed Northern blot analysis in accordance with the standard protocol described in the manual.

Specifically, the area of pLKB-1 which included the coding region was excised with restriction enzymes and purified by agarose gel electrophoresis. The pure product was labelled with [α-$^{32}$P]dCTP by the standard random hexamer method using the Ready to Go DNA labelling beads purchased from Pharmacia. After thermal denaturation, the labelled clone was warmed in ExpressHyb Hybridization Solution (purchased from CLONTECH) at 68° C. together with a selected membrane to thereby effect hybridization. After the hybridization, the clone was washed with 2×SSC and 0.1% SDS several times at room temperature, followed by two washings with 0.1×SSC and 0.1% SDS at 50° C. for 20 min. The membrane was dried and then subjected to autoradiography. The results are shown in FIG. 1.

In almost all of the tissues investigated, weak expression of about 3 kbp occurred, except that a stronger expression occurred in HL-60 cells, with a fairly strong expression being observed in adult testis, adult skeletal muscle, fetal liver and K562 cells.

INDUSTRIAL APPLICABILITY

The protein kinase coding DNA of the invention is a novel clone that has not been known to date.

The DNA of the invention is believed to encode protein knases, in particular, serine/threonine protein kinase and it has been found to have comparatively high levels of homology to AMPK and MAP kinase as demonstrated by the homology search the results of which have been described in the Example.

AMPK is known to be a kinase taking part in the regulation of the metabolism of lipids or sugars and the protein kinase encoded by the novel DNA sequence of the invention also has the potential to work as a factor taking part in the same kind of metabolic regulation. On the other hand, MAP kinase is known to be a factor that plays an important role in the kinase cascade for intracellular signal transduction from receptors such as ones of cell growth factors and, hence, the protein kinase encoded by the novel DNA sequence of the invention also has the potential to take part in such kinase cascade.

Thus, the protein kinase encoded by the novel DNA of the invention is believed to take part in the regulation of certain cell functions. Therefore, therapeutic methods effective against diseases due to abnormal activities of the protein kinase of the invention can potentially be offered by taking various approaches, such as (1) suppressing the in vivo expression of the gene of interest by administering an antisense DNA or RNA or the like that are based on the base sequence of that gene, (2) introducing the gene of interest into the human body as it is incorporated into a suitable vector such as a retroviral vector, (3) developing drugs, which act on transfer regulating factors which regulate in vivo expression of the gene of interest and/or a promoter and the like of the same gene, and (4) developing drugs which either suppress or promote the activities of the protein kinase encoded by the gene of interest.

As FIG. 1 shows, a particularly strong expression occurred in several tissues and it is well known that in such tissues, highly undifferentiated cells capable of autoreproduction such as blood stem cells in the fetal liver occur to take on a "stem cell system". Being leukemia cells, HL-60 and K562 cells are believed to maintain a comparatively undifferentiated state and it is also well known that they can be induced to become differentiated in response to certain kinds of stimulant. On the other hand, the leukocyte fractions of peripheral blood which are also blood cells but are believed to be in a differentiated state allow for only a faint expression of the gene of interest. Thus, the gene of interest has a characteristic expression pattern in that a very strong expression occurs in undifferentiated cells or in tissues abundant with undifferentiated cells but that a very weak expression occurs in differentiated cells. This suggests the possibility that the kinase encoded by the gene of interest phosphorylates a certain substrate protein to control the differentiation of cells. Further, one could induce the differentiation of undifferentiated cells by inhibiting the activity of the kinase which is highly expressed in those cells. It is well known that certain kinds of cancer cells can be treated by differentiation inducing therapy using suitable agents such as retinoic acid. Therefore, the development of an inhibitor of the kinase might contribute to combatting cancers using that inhibitor.

I claim:

1. An isolated DNA encoding a protein having a protein kinase activity, comprising a base sequence encoding the amino acid sequence of SEQ ID NO:7, or a base sequence encoding a protein kinase which hybridizes with said base sequence encoding the amino acid sequence of SEQ ID NO:7 in a solution of 0.2×SSC and 0.1% SDS at 60° C.

2. An isolated DNA according to claim 1, comprising the base sequence of SEQ ID NO:2.

3. A plasmid having the DNA of claim 1.

4. A transformant obtained by transforming a prokaryotic or eukaryotic cell with the plasmid of claim 3.

5. An oligonucleotide which hybridizes with a base sequence encoding the amino acid sequence of SEQ ID NO:7 in a solution of 0.2×SSC and 0.1% SDS at 60° C.

6. An isolated DNA encoding a protein having a protein kinase activity, comprising a base sequence encoding the amino acid sequence of SEQ ID NO:7, or a base sequence encoding a protein kinase which hybridizes with said base sequence encoding the amino acid sequence of SEQ ID NO:7 in a solution of 50% formamide, 4×SSC, 50 mM HEPES, pH 7.0, 10×Denhardt's solution, 100 µg/ml thermally denatured salmon sperm DNA at 42° C.

7. An isolated DNA according to claim 6, comprising the base sequence of SEQ ID NO: 2.

8. A plasmid comprising the isolated DNA of claim 6.

9. A transformant obtained by transforming a prokaryotic or eukaryotic cell with the plasmid of claim 8.

10. An oligonucleotide which hybridizes with a base sequence encoding the amino acid sequence of SEQ ID NO: 7 in a solution of 50% formamide, 4×SSC, 50 mM HEPES, pH 7.0, 10×Denhardt's solution, 100 µg/ml thermally denatured salmon sperm DNA at 42° C.

* * * * *

UNITED STATES PATENT AND TRADEMARK OFFICE
CERTIFICATE OF CORRECTION

PATENT NO. : 5,827,726
DATED : Oct. 27, 1998
INVENTOR(S) : Nezu

It is certified that error appears in the above-identified patent and that said Letters Patent is hereby corrected as shown below:

```
    Cover page, in the title at line [54], delete
"Coding" and insert therefor --Encoding--;
    Column 1, line 1, in the title, delete "Coding"
and insert therefor --Encoding--.
```

Signed and Sealed this

Twenty-fifth Day of May, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 186 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

| GTT | GCG | GTT | AAG | ATG | TTG | AAG | AAG | AAG | AAG | TTG | CGA | AGG | ATC | CCC | AAC | 4 8 |
|-----|-----|-----|-----|-----|-----|-----|-----|-----|-----|-----|-----|-----|-----|-----|-----|-----|
| Val | Ala | Val | Lys | Met | Leu | Lys | Lys | Lys | Lys | Leu | Arg | Arg | Ile | Pro | Asn | |
| 1 | | | | 5 | | | | | 10 | | | | | 15 | | |

| GGG | GAG | GCC | AAC | GTG | AAG | AAG | GAA | ATT | CAA | CTA | CTG | AGG | AGG | TTA | CGG | 9 6 |
|-----|-----|-----|-----|-----|-----|-----|-----|-----|-----|-----|-----|-----|-----|-----|-----|-----|
| Gly | Glu | Ala | Asn | Val | Lys | Lys | Glu | Ile | Gln | Leu | Leu | Arg | Arg | Leu | Arg | |
| | | | 20 | | | | | 25 | | | | 30 | | | | |

| CAC | AAA | AAT | GTC | ATG | CAG | CTG | GTG | GAT | GTG | TTA | TAC | AAC | GAA | GAG | AAG | 1 4 4 |

| | | | | | | | | | | | | | | | | |
|---|---|---|---|---|---|---|---|---|---|---|---|---|---|---|---|---|
|His|Lys|Asn|Val|Met|Gln|Leu|Val|Asp|Val|Leu|Tyr|Asn|Glu|Glu|Lys| |
| | |35| | | |40| | | |45| | | | | | |

| CAG | AAA | ATG | TAT | ATG | GTG | ATG | GAA | TAC | TGC | TGC | TAC | GGC | GAG | 186 |
|---|---|---|---|---|---|---|---|---|---|---|---|---|---|---|
| Gln | Lys | Met | Tyr | Met | Val | Met | Glu | Tyr | Cys | Cys | Tyr | Gly | Glu | |
| | 50 | | | | | 55 | | | | 60 | | | | |

(2) INFORMATION FOR SEQ ID NO:2:

(i) SEQUENCE CHARACTERISTICS:
        (A) LENGTH: 1302 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| ATG | GAG | GTG | GTG | GAC | CCG | CAG | CAG | CTG | GGC | ATG | TTC | ACG | GAG | GGC | GAG | 48 |
|---|---|---|---|---|---|---|---|---|---|---|---|---|---|---|---|---|
| Met | Glu | Val | Val | Asp | Pro | Gln | Gln | Leu | Gly | Met | Phe | Thr | Glu | Gly | Glu | |
| | | | | 5 | | | | | 10 | | | | | 15 | | |

| CTG | ATG | TCG | GTG | GGT | ATG | GAC | ACG | TTC | ATC | CAC | CGC | ATC | GAC | TCC | ACC | 96 |
|---|---|---|---|---|---|---|---|---|---|---|---|---|---|---|---|---|
| Leu | Met | Ser | Val | Gly | Met | Asp | Thr | Phe | Ile | His | Arg | Ile | Asp | Ser | Thr | |
| | | | 20 | | | | | 25 | | | | | 30 | | | |

| GAG | GTC | ATC | TAC | CAG | CCG | CGC | CGC | AAG | CGG | GCC | AAG | CTC | ATC | GGC | AAG | 144 |
|---|---|---|---|---|---|---|---|---|---|---|---|---|---|---|---|---|
| Glu | Val | Ile | Tyr | Gln | Pro | Arg | Arg | Lys | Arg | Ala | Lys | Leu | Ile | Gly | Lys | |
| | | | 35 | | | | 40 | | | | | 45 | | | | |

| TAC | CTG | ATG | GGG | GAC | CTG | CTG | GGG | GAA | GGC | TCT | TAC | GGC | AAG | GTG | AAG | 192 |
|---|---|---|---|---|---|---|---|---|---|---|---|---|---|---|---|---|
| Tyr | Leu | Met | Gly | Asp | Leu | Leu | Gly | Glu | Gly | Ser | Tyr | Gly | Lys | Val | Lys | |
| | | 50 | | | | | 55 | | | | | 60 | | | | |

| GAG | GTG | CTG | GAC | TCG | GAG | ACG | CTG | TGC | AGG | AGG | GCC | GTC | AAG | ATC | CTC | 240 |
|---|---|---|---|---|---|---|---|---|---|---|---|---|---|---|---|---|
| Glu | Val | Leu | Asp | Ser | Glu | Thr | Leu | Cys | Arg | Arg | Ala | Val | Lys | Ile | Leu | |
| 65 | | | | | 70 | | | | | 75 | | | | | 80 | |

| AAG | AAG | AAG | AAG | TTG | CGA | AGG | ATC | CCC | AAC | GGG | GAG | GCC | AAC | GTG | AAG | 288 |
|---|---|---|---|---|---|---|---|---|---|---|---|---|---|---|---|---|
| Lys | Lys | Lys | Lys | Leu | Arg | Arg | Ile | Pro | Asn | Gly | Glu | Ala | Asn | Val | Lys | |
| | | | | 85 | | | | | 90 | | | | | 95 | | |

| AAG | GAA | ATT | CAA | CTA | CTG | AGG | AGG | TTA | CGG | CAC | AAA | AAT | GTC | ATC | CAG | 336 |
|---|---|---|---|---|---|---|---|---|---|---|---|---|---|---|---|---|
| Lys | Glu | Ile | Gln | Leu | Leu | Arg | Arg | Leu | Arg | His | Lys | Asn | Val | Ile | Gln | |
| | | | 100 | | | | 105 | | | | | 110 | | | | |

| CTG | GTG | GAT | GTG | TTA | TAC | AAC | GAA | GAG | AAG | CAG | AAA | ATG | TAT | ATG | GTG | 384 |
|---|---|---|---|---|---|---|---|---|---|---|---|---|---|---|---|---|
| Leu | Val | Asp | Val | Leu | Tyr | Asn | Glu | Glu | Lys | Gln | Lys | Met | Tyr | Met | Val | |
| | | 115 | | | | | 120 | | | | | 125 | | | | |

| ATG | GAG | TAC | TGC | GTG | TGT | GGC | ATG | CAG | GAA | ATG | CTG | GAC | AGC | GTG | CCG | 432 |
|---|---|---|---|---|---|---|---|---|---|---|---|---|---|---|---|---|
| Met | Glu | Tyr | Cys | Val | Cys | Gly | Met | Gln | Glu | Met | Leu | Asp | Ser | Val | Pro | |
| 130 | | | | | | 135 | | | | | 140 | | | | | |

| GAG | AAG | CGT | TTC | CCA | GTG | TGC | CAG | GCC | CAC | GGG | TAC | TTC | TGT | CAG | CTG | 480 |
|---|---|---|---|---|---|---|---|---|---|---|---|---|---|---|---|---|
| Glu | Lys | Arg | Phe | Pro | Val | Cys | Gln | Ala | His | Gly | Tyr | Phe | Cys | Gln | Leu | |
| 145 | | | | | 150 | | | | | 155 | | | | | 160 | |

| ATT | GAC | GGC | CTG | GAG | TAC | CTG | CAT | AGC | CAG | GGC | ATT | GTG | CAC | AAG | GAC | 528 |
|---|---|---|---|---|---|---|---|---|---|---|---|---|---|---|---|---|
| Ile | Asp | Gly | Leu | Glu | Tyr | Leu | His | Ser | Gln | Gly | Ile | Val | His | Lys | Asp | |
| | | | | 165 | | | | | 170 | | | | | 175 | | |

| ATC | AAG | CCG | GGG | AAC | CTG | CTG | CTC | ACC | ACC | GGT | GGC | ACC | CTC | AAA | ATC | 576 |
|---|---|---|---|---|---|---|---|---|---|---|---|---|---|---|---|---|
| Ile | Lys | Pro | Gly | Asn | Leu | Leu | Leu | Thr | Thr | Gly | Gly | Thr | Leu | Lys | Ile | |
| | | | 180 | | | | | 185 | | | | | 190 | | | |

| TCC | GAC | CTG | GGC | GTG | GCC | GAG | GCA | CTG | CAC | CCG | TTC | GCG | GCG | GAC | GAC | 624 |
|---|---|---|---|---|---|---|---|---|---|---|---|---|---|---|---|---|
| Ser | Asp | Leu | Gly | Val | Ala | Glu | Ala | Leu | His | Pro | Phe | Ala | Ala | Asp | Asp | |
| | | | 195 | | | | | 200 | | | | | 205 | | | |

| ACC | TGC | CGG | ACC | AGC | CAG | GGC | TCC | CCG | GCT | TTC | CAG | CCG | CCC | GAG | ATT | 672 |
|---|---|---|---|---|---|---|---|---|---|---|---|---|---|---|---|---|
| Thr | Cys | Arg | Thr | Ser | Gln | Gly | Ser | Pro | Ala | Phe | Gln | Pro | Pro | Glu | Ile | |
| | 210 | | | | | 215 | | | | | 220 | | | | | |

| GCC | AAC | GGC | CTG | GAC | ACC | TTC | TCC | GGC | TTC | AAG | GTG | GAC | ATC | TGG | TCG | 720 |
|---|---|---|---|---|---|---|---|---|---|---|---|---|---|---|---|---|
| Ala | Asn | Gly | Leu | Asp | Thr | Phe | Ser | Gly | Phe | Lys | Val | Asp | Ile | Trp | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GCT | GGG | GTC | ACC | CTC | TAC | AAC | ATC | ACC | ACG | GGT | CTG | TAC | CCC | TTC | GAA | 768 |
| Ala | Gly | Val | Thr | Leu | Tyr | Asn | Ile | Thr | Thr | Gly | Leu | Tyr | Pro | Phe | Glu | |
| | | | | 245 | | | | | 250 | | | | | 255 | | |
| GGG | GAC | AAC | ATC | TAC | AAG | TTG | TTT | GAG | AAC | ATC | GGG | AAG | GGG | AGC | TAC | 816 |
| Gly | Asp | Asn | Ile | Tyr | Lys | Leu | Phe | Glu | Asn | Ile | Gly | Lys | Gly | Ser | Tyr | |
| | | | 260 | | | | | 265 | | | | | 270 | | | |
| GCC | ATC | CCG | GGC | GAC | TGT | GGC | CCC | CCG | CTC | TCT | GAC | CTG | CTG | AAA | GGG | 864 |
| Ala | Ile | Pro | Gly | Asp | Cys | Gly | Pro | Pro | Leu | Ser | Asp | Leu | Leu | Lys | Gly | |
| | | 275 | | | | | 280 | | | | | 285 | | | | |
| ATG | CTT | GAG | TAC | GAA | CCG | GCC | AAG | AGG | TTC | TCC | ATC | CGG | CAG | ATC | CGG | 912 |
| Met | Leu | Glu | Tyr | Glu | Pro | Ala | Lys | Arg | Phe | Ser | Ile | Arg | Gln | Ile | Arg | |
| | 290 | | | | 295 | | | | | 300 | | | | | | |
| CAG | CAC | AGC | TGG | TTC | CGG | AAG | AAA | CAT | CCT | CCG | GCT | GAA | GCA | CCA | GTG | 960 |
| Gln | His | Ser | Trp | Phe | Arg | Lys | Lys | His | Pro | Pro | Ala | Glu | Ala | Pro | Val | |
| 305 | | | | 310 | | | | | 315 | | | | | 320 | | |
| CCC | ATC | CCA | CCG | AGC | CCA | GAC | ACC | AAG | GAC | CGG | TGG | CGC | AGC | ATG | ACT | 1008 |
| Pro | Ile | Pro | Pro | Ser | Pro | Asp | Thr | Lys | Asp | Arg | Trp | Arg | Ser | Met | Thr | |
| | | | | 325 | | | | 330 | | | | | 335 | | | |
| GTG | GTG | CCG | TAC | TTG | GAG | GAC | CTG | CAC | GGC | GCG | GAC | GAG | GAC | GAG | GAC | 1056 |
| Val | Val | Pro | Tyr | Leu | Glu | Asp | Leu | His | Gly | Ala | Asp | Glu | Asp | Glu | Asp | |
| | | | 340 | | | | | 345 | | | | | 350 | | | |
| CTC | TTC | GAC | ATC | GAG | GAT | GAC | ATC | ATC | TAC | ACT | CAG | GAC | TTC | ACG | GTG | 1104 |
| Leu | Phe | Asp | Ile | Glu | Asp | Asp | Ile | Ile | Tyr | Thr | Gln | Asp | Phe | Thr | Val | |
| | | 355 | | | | | 360 | | | | | 365 | | | | |
| CCC | GGA | CAG | GTC | CCA | GAA | GAG | GAG | GCC | AGT | CAC | AAT | GGA | CAG | CGC | CGG | 1152 |
| Pro | Gly | Gln | Val | Pro | Glu | Glu | Glu | Ala | Ser | His | Asn | Gly | Gln | Arg | Arg | |
| | 370 | | | | 375 | | | | | 380 | | | | | | |
| GGC | CTC | CCC | AAG | GCC | GTG | TGT | ATG | AAC | GGC | ACA | GAG | GCG | GCG | CAG | CTG | 1200 |
| Gly | Leu | Pro | Lys | Ala | Val | Cys | Met | Asn | Gly | Thr | Glu | Ala | Ala | Gln | Leu | |
| 385 | | | | 390 | | | | | 395 | | | | | 400 | | |
| AGC | ACC | AAA | TCC | AGG | GCG | GAG | GGC | CGG | GCC | CCC | AAC | CCT | GCC | CGC | AAG | 1248 |
| Ser | Thr | Lys | Ser | Arg | Ala | Glu | Gly | Arg | Ala | Pro | Asn | Pro | Ala | Arg | Lys | |
| | | | | 405 | | | | 410 | | | | | 415 | | | |
| GCC | TGC | TCC | GCC | AGC | AGC | AAG | ATC | CGC | CGG | CTG | TCG | GCC | TGC | AAG | CAG | 1296 |
| Ala | Cys | Ser | Ala | Ser | Ser | Lys | Ile | Arg | Arg | Leu | Ser | Ala | Cys | Lys | Gln | |
| | | | 420 | | | | | 425 | | | | | 430 | | | |
| CAG | TGA | | | | | | | | | | | | | | | 1302 |
| Gln | | | | | | | | | | | | | | | | |

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GTNGCNGTNA ARATGYTNAA         20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TCNCCRTARC ARCARTAYTC         20

( 2 ) INFORMATION FOR SEQ ID NO:5:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

```
TGAAGAAGAA GAAGTTGCGA AGGA                                              24
```

( 2 ) INFORMATION FOR SEQ ID NO:6:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:6:

```
CCACCAGCTG GATGACATTT TTGT                                              24
```

( 2 ) INFORMATION FOR SEQ ID NO:7:

( i ) SEQUENCE CHARACTERISTICS:
    ( A ) LENGTH: 433 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

```
Met  Glu  Val  Val  Asp  Pro  Gln  Gln  Leu  Gly  Met  Phe  Thr  Glu  Gly  Glu
                    5                   10                      15
Leu  Met  Ser  Val  Gly  Met  Asp  Thr  Phe  Ile  His  Arg  Ile  Asp  Ser  Thr
               20                   25                      30
Glu  Val  Ile  Tyr  Gln  Pro  Arg  Arg  Lys  Arg  Ala  Lys  Leu  Ile  Gly  Lys
               35                   40                      45
Tyr  Leu  Met  Gly  Asp  Leu  Leu  Gly  Glu  Gly  Ser  Tyr  Gly  Lys  Val  Lys
     50                        55                 60
Glu  Val  Leu  Asp  Ser  Glu  Thr  Leu  Cys  Arg  Arg  Ala  Val  Lys  Ile  Leu
65                        70                  75                            80
Lys  Lys  Lys  Lys  Leu  Arg  Arg  Ile  Pro  Asn  Gly  Glu  Ala  Asn  Val  Lys
                    85                   90                      95
Lys  Glu  Ile  Gln  Leu  Leu  Arg  Arg  Leu  Arg  His  Lys  Asn  Val  Ile  Gln
               100                  105                     110
Leu  Val  Asp  Val  Leu  Tyr  Asn  Glu  Glu  Lys  Gln  Lys  Met  Tyr  Met  Val
               115                  120                     125
Met  Glu  Tyr  Cys  Val  Cys  Gly  Met  Gln  Glu  Met  Leu  Asp  Ser  Val  Pro
     130                       135                140
Glu  Lys  Arg  Phe  Pro  Val  Cys  Gln  Ala  His  Gly  Tyr  Phe  Cys  Gln  Leu
145                       150                  155                           160
Ile  Asp  Gly  Leu  Glu  Tyr  Leu  His  Ser  Gln  Gly  Ile  Val  His  Lys  Asp
                    165                 170                     175
Ile  Lys  Pro  Gly  Asn  Leu  Leu  Leu  Thr  Thr  Gly  Gly  Thr  Leu  Lys  Ile
               180                  185                     190
```

Ser Asp Leu Gly Val Ala Glu Ala Leu His Pro Phe Ala Ala Asp Asp
    195             200             205

Thr Cys Arg Thr Ser Gln Gly Ser Pro Ala Phe Gln Pro Pro Glu Ile
    210             215             220

Ala Asn Gly Leu Asp Thr Phe Ser Gly Phe Lys Val Asp Ile Trp Ser
225             230             235             240

Ala Gly Val Thr Leu Tyr Asn Ile Thr Thr Gly Leu Tyr Pro Phe Glu
            245             250             255

Gly Asp Asn Ile Tyr Lys Leu Phe Glu Asn Ile Gly Lys Gly Ser Tyr
            260             265             270

Ala Ile Pro Gly Asp Cys Gly Pro Pro Leu Ser Asp Leu Leu Lys Gly
            275             280             285

Met Leu Glu Tyr Glu Pro Ala Lys Arg Phe Ser Ile Arg Gln Ile Arg
    290             295             300

Gln His Ser Trp Phe Arg Lys Lys His Pro Pro Ala Glu Ala Pro Val
305             310             315             320

Pro Ile Pro Pro Ser Pro Asp Thr Lys Asp Arg Trp Arg Ser Met Thr
            325             330             335

Val Val Pro Tyr Leu Glu Asp Leu His Gly Ala Asp Glu Asp Glu Asp
            340             345             350

Leu Phe Asp Ile Glu Asp Asp Ile Ile Tyr Thr Gln Asp Phe Thr Val
            355             360             365

Pro Gly Gln Val Pro Glu Glu Glu Ala Ser His Asn Gly Gln Arg Arg
    370             375             380

Gly Leu Pro Lys Ala Val Cys Met Asn Gly Thr Glu Ala Ala Gln Leu
385             390             395             400

Ser Thr Lys Ser Arg Ala Glu Gly Arg Ala Pro Asn Pro Ala Arg Lys
            405             410             415

Ala Cys Ser Ala Ser Ser Lys Ile Arg Arg Leu Ser Ala Cys Lys Gln
            420             425             430

Gln ( 2 ) INFORMATION FOR SEQ ID NO:8:

( i ) SEQUENCE CHARACTERISTICS:
        ( A ) LENGTH: 62 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Val Ala Val Lys Met Leu Lys Lys Lys Leu Arg Arg Ile Pro Asn
1               5               10              15

Gly Glu Ala Asn Val Lys Lys Glu Ile Gln Leu Leu Arg Arg Leu Arg
            20              25              30

His Lys Asn Val Met Gln Leu Val Asp Val Leu Tyr Asn Glu Glu Lys
            35              40              45

Gln Lys Met Tyr Met Val Met Glu Tyr Cys Cys Tyr Gly Glu
    50              55              60

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
                ( D ) OTHER INFORMATION: Xaa in position 1 is Leu, Ile or Val
                        Xaa in positions 3 and 5 are any amino acid
                        Xaa in position 6 is Phe, Tyr or Met
                        Xaa in position 7 is Ser or Gly
                        Xaa in position 8 is any amino acid ( x i ) SEQUENCE DESCRIPTION: SEQ ID NO:9:

Xaa  Gly  Xaa  Gly  Xaa  Xaa  Xaa  Xaa  Val
                         5

( 2 ) INFORMATION FOR SEQ ID NO:10:

( i ) SEQUENCE CHARACTERISTICS:
                ( A ) LENGTH: 13 amino acids
                ( B ) TYPE: amino acid
                ( C ) STRANDEDNESS: single
                ( D ) TOPOLOGY: linear ( i i ) MOLECULE TYPE: peptide ( i x ) FEATURE:
                ( D ) OTHER INFORMATION: Xaa in position 1 is Leu, Ile, Val,
                        Met, Phe, Tyr or Cys
                        Xaa in position 2 is any amino acid
                        Xaa in position 3 is His or Tyr
                        Xaa in position 4 is any amino acid
                        Xaa in position 6 is Leu, Ile, Val, Met, Phe or Tyr
                        Xaa in positions 8 and 9 are any amino acid
                        Xaa in positions 11-13 are Leu, Ile, Val, Met, Phe,
                        Tyr or Cys ( x i ) SEQUENCE DESCRIPTION: SEQ ID NO:10:

Xaa  Xaa  Xaa  Xaa  Asp  Xaa  Lys  Xaa  Xaa  Asn  Xaa  Xaa  Xaa
                         5                           10